US008394629B2

(12) United States Patent
Umezawa et al.

(10) Patent No.: US 8,394,629 B2
(45) Date of Patent: Mar. 12, 2013

(54) USE OF VINCA ALKALOIDS AND SALTS THEREOF

(75) Inventors: Kazuo Umezawa, Tokyo (JP); Hisako Ohgawara, Tokyo (JP); Itaru Kojima, Maebashi (JP); Takashi Koyano, Tokyo (JP)

(73) Assignee: Keio University, Tokyo (JP)

( * ) Notice: Subject to any disclaimer, the term of this patent is extended or adjusted under 35 U.S.C. 154(b) by 439 days.

(21) Appl. No.: 12/477,333

(22) Filed: Jun. 3, 2009

(65) Prior Publication Data

US 2009/0239301 A1    Sep. 24, 2009

Related U.S. Application Data

(62) Division of application No. 10/556,309, filed on Nov. 3, 2006, now abandoned.

(30) Foreign Application Priority Data

May 9, 2003    (JP) .................................. 2003-131256
Oct. 31, 2003    (JP) .................................. 2003-373665

(51) Int. Cl.
*C12N 5/00*    (2006.01)
(52) U.S. Cl. ........................................................ 435/377
(58) Field of Classification Search ........................ None
See application file for complete search history.

(56) References Cited

FOREIGN PATENT DOCUMENTS

| JP | 11-322602 | 11/1999 |
| JP | 2002-543164 | 11/2000 |
| JP | 2003-113111 A | 4/2003 |
| JP | 2004-121165 A | 4/2004 |

OTHER PUBLICATIONS

Mashima et al (J Clin Invest 97:1647-1654, 1996).*
Otonkoski et al (J Clin Invest 92:1459-1466, 1993).*
Bergsten et al (J Endocrinol 158:115-120, 1998).*
Shima, Kenji, et al., "A Role of Nicotinamide-induced Increase in Pancreatic β-cell Mass on Blood Glucose Control After Discontinuation of the Treatment in Partially Pancreatectomized OLETF Rats", Diabetes Research and Clinical Practice 41 (1998) pp. 1-8.
Akiyama et al., "Activation of *Reg* Gene, a Gene for Insulin-Producing β-Cell Regeneration: Poly(ADP-ribose) Polymerase Binds *Reg* Promoter and Regulates the Transcription by Autopoly(ADP-ribosyl)ation," Proc. Natl. Acad. Sci. USA, vol. 98, No. 1, Jan. 2, 2001, pp. 48-53.
Assady et al., "Insulin Production by Human Embryonic Stem Cells," *Diabetes*, vol. 50, Aug. 2001, pp. 1691-1697.
Bonner-Weir et al., "A Second Pathway for Regeneration of Adult Exocrine and Endocrine Pancreas," *Diabetes*, vol. 42, Dec. 1993, pp. 1715-1720.
Bonner-Weir et al., "In Vitro Cultivation of Human Islets from Expanded Ductal Tissue," Proc. Nat. Acad. Sci. USA, vol. 97, No. 14, Jul. 5, 2000, pp. 7999-8004.
Demeterco et al., "A Role for Active A and Betacelluln in Human Fetal Pancreatic Cell Differentiation and Growth," *The Journal of Clinical Endocrinology & Metabolism*, vol. 85, No. 10, 2000, pp. 3892-3897.
Garcia-Ocaña A, Takane KK, Syed MA, Philbrick WM, Vasavada RC, Stewart AF, "Hepatocyte growth factor overexpression in the islet of transgenic mice increases beta cell proliferation, enhances islet mass, and induces mild hypoglycemia," J Biol Chem vol. 275, No. 2, pp. 1226-1232, Jan. 2000.
Herrera, "Adult Insulin- and Glucagon-Producing Cells Differentiate From Two Independent Cell Lineages," *Development*, 127, 2000, pp. 2317-2322.
Hiroki et al., "Conophylline-Induced Insulin Production in Rat Pancreatic Acinar Carcinoma Cells," 61st Annual Meeting of the American Diabetes Association, 2001, Abstract (1 page).
Hiroki et al., "Induction of Insulin Production in Rat Pancreatic Cells by the Vinca Alkaloid Conophylline," 44th Annual Meeting of the Japan Diabetes Society, 2001, Abstract (3 pages).
Hiroki et al., "Mechanism of Inducing Insulin Production in Rat Pancreatic Acinar Carcinoma Cells by Conophylline," *Journal of the Japan Diabetes Society*, vol. 45, Supplement 2: II-G502-1-2, 2002 (5 pages).
Hunziker et al., "Nestin-Expressing Cells in the Pancreatic Islets of Langerhans," *Biochemical and Biophysical Research Communications* 271, 2000, pp. 116-119.
Ishiyama et al., "Studies on the Betacellulin Receptor in Pancreatic AR42J Cells," *Diabetologia*, vol. 41, 1998, pp. 623-628.
Kam et al., "Alkaloids From *Tabernaemontana divaricata*," *Phytochemistry*, vol. 40, No. 1, 1995, pp. 313-316.
Kam et al., "Conophylline and Conophyllidine: New Dimeric Alkaloids from *Tabernaemontana divaricata*," *Journal of Natural Products*, vol. 56, No. 11, Nov. 1993, pp. 1865-1871.
Kam TH, Pang HS, and Lim TM, "Biologically active indole and bisindole alkaloids from *Tabernaemontana divaricata*," Org Biomol Chem, vol. 1, pp. 1292-1297, 2003.
Kawakami et al., "Induction of Differentiation of Neonatal Porcine Pancreatic Cells into Insulin-Producing Cells by the Vinca Alkaloid Conophylline," 47th Annual Meeting of the Japan Diabetes Society, 2004, Abstract (5 pages).
Kawakami et al., "Induction of Insulin Production by Plant-Derived Conophylline in Newborn Porcine Pancreatic Cells," 3rd Annual Congress of the Japan Society for Regenerative Medicine, 2004, Abstract (4 pages).
Kawakami et al., "Induction of Insulin Production in Rat Pancreatic Acinar Carcinoma Cells by Conophylline and Related Vinca Alkaloids," 18th International Diabetes Federation Congress, Paris, France, Aug. 24-29, 2003 (1 page).
Kawakmi et al., "Differentiation into Pancreatic Endocrine Cells by Using the Three-Dimensional Tissue Culture System of Neonatal Porcine Pancreatic Duct," 46th Annual Meeting of the Japan Diabetes Society, 2003, Abstract (6 pages).

(Continued)

*Primary Examiner* — Craig Ricci
(74) *Attorney, Agent, or Firm* — Finnegan, Henderson, Farabow, Garrett & Dunner, L.L.P.

(57) ABSTRACT

An agent containing a vinca alkaloid or its pharmacologically acceptable salt as an active ingredient can induce insulin production and/or secretion of non-neoplastic cells derived from the pancreas.

4 Claims, 4 Drawing Sheets

OTHER PUBLICATIONS

Kodera et al., "Induction of β Cell Differentiation by Conophylline and Betacellulin-δ4," *Journal of the Japan Diabetes Society*, vol. 47, Supplement 1: III-G510-19, 2004 (5 pages).

Kodera et al., "Induction of β Cell Differentiation by Conophylline and Betacellulin-δ4," 77th Annual Meeting of the Japan Endocrine Society, 2004, Abstract (3 pages).

Korsgren et al., "In Vitro Screening of Putative Compounds Inducing Fetal Porcine Pancreatic β-Cell Differentiation: Implications for Cell Transplantation in Insulin-Dependent Diabetes Mellitus," *Upsala J. Med. Sci.*, vol. 98, 1993, pp. 39-52.

Lumelsky et al., "Differentiation of Embryonic Stem Cells to Insulin-Secreting Structures Similar to Pancreatic Islets," *Science*, vol. 292, May 18, 2001, pp. 1389-1394.

Mashima et al. (Diabetes 50:S39-S40, 2001).

Merriam-Webster Online Dictionary (accessed Jan. 27, 2009).

Montori et al. (BMJ 334:882-884, 2007).

Nadya Lumelsky, Olivier Blondel, Pascal Laeng, Ivan Velasco, Rea Ravin, Ron McKay, "Differentiation of Embryonic Stem Cells to Insulin-Secreting Structures Similar to Pancreatic Islets Science," vol. 292, No. 5520, pp. 1389-1394, 2001.

Neuss et al, Vinca Alkaloids. XXI. The Structures of the Oncolytic Alkaloids Vinblastine (VLB) and Vincristine (VCR), *Journal of Am. Chem. Soc.*, vol. 86, 1964, pp. 1440-1442.

Ogata et al., "Induction of Differentiation from Pancreatic Stem Cells into β Cells by the Vinca Alkaloid Conophylline," *Journal of the Japan Diabetes Society*, vol. 45, Supplement 2: III-D-4, 2002 (4 pages).

Ogata et al., "Induction of Differentiation into Insulin-Producing Cells by Betacellulin-δ4 and Conophylline," *Journal of the Japan Diabetes Society*, vol. 46, Supplement 1: I-CI-15, 2003 (5 pages).

Ogata et al., "Prevention of Onset of Type 2 Diabetes by Conophylline and Betacellulin-δ4," 46th Annual Meeting of the Japan Diabetes Society, 2003, Abstract (2 pages).

Ogata et al., "Promotion of differentiation of the pancreatic progenitor cells into beta cells by conophylline," 62nd Annual Meeting of the American Diabetes Association, 2002.

Ohgawara et al., "Diabetes Mellitus: Rational Basis, Clinical Approach and Future Therapy," Biomedicine & Pharmacotherapy 58 (2004) pp. 605-609.

Otonkoski T, Beattie GM, Mally MI, Ricordi C, Hayek A. Nicotinamide is a potent inducer of endocrine differentiation in cultured human fetal pancreatic cells. J Clin Invest 92(3):1459-66, 1993.

Ramiya et al., "Reversal of Insulin-Dependent Diabetes Using Islets Generated In Vitro from Pancreatic Stem Cells," *Nature Medicine*, vol. 6, No. 3, Mar. 2000, pp. 278-282.

Sjöholm et al., "Polyamine Requirements in Nicotinamide-Stimulated β-Cell Differentiation in Fetal Porcine Islet-Like Cell Clusters," *Endocrinology*, vol. 135, No. 4, 1994, pp. 1559-1565.

Supplementary Partial European Search Report mailed Mar. 3, 2008.

Takatsuna et al., "Screening of Bioactive Metabolites for Pancreatic Regeneration Chemotherapy," Biomedicine & Pharmacotherapy 58 (2004) pp. 610-613.

Umezawa et al., "Growth Inhibition of K-*RAS*-Expressing Tumours by a New Vinca Alkaloid, Conophyline, in Nude Mice," Drugs Exptl. Clin. Res. 22: (1996), pp. 35-40.

Umezawa et al., "Induction of Differentiation into Insulin-Producing Cells by Physiologically Active Substances," 24th Annual Meeting of the Japanese Society of Inflammation and Regeneration, 2003, Abstract (3 pages).

Umezawa et al., "Induction of Differentiation into Insulin-Producing Cells by the Plant-Derived Vinca Alkaloid Conophylline," 6th Annual Meeting of the Japanese Society for Tissue Engineering, 2003, Abstract (3 pages).

Umezawa et al., "Isolation of a New Vinca Alkaloid from the Leaves of *Ervatamia microphylla* as an Inhibitor of *ras* Functions," *Anticancer Research*, 14: 1994, pp. 2413-2417.

Umezawa K, Hiroki A, Kawakami M, Naka H, Takei I, Ogata T, Kojima I, Koyano T, Kowithayakorn T, Pang HS, Kam TS. Induction of insulin production in rat pancreatic acinar carcinoma cells by conophyline. Biomed Pharmacother 57(8):341-51, 2003.

Umezawa, "Chemical Biology and Searches for Anticancer Agents and Antidiabetic Agents," 1st ChemBio Symposium, 2004, Abstract (6 pages).

Umezawa, "Induction of Insulin Production in Rat Pancreatic Acinar Carcinoma Cells by Conophylline Isolated from *Ervatamia microphylla*," 3rd International Symposium on Natural Drugs, Naples, Oct. 2-4, 2003, p. 59.

Umezawa, "Induction of P38-Mediated Insulin Production in Pancreatic Acinar Carcinoma Cells by the Alkaloid Conophylline," 38th Annual Meeting of the European Association for the Study of the Diabetes (EASD), 2002, Abstract (1 page).

Umezawa, "Search of Signal Transduction Inhibitors and Modification of the Blood Vessel Wall Function," Public Symposium "Development of Artificial Techniques for Controlling Function of Blood Vessel Wall," 2005, Abstract (5 pages).

Umezawa, Chapter 15, Decomposition and Regeneration by Microorganisms, "Regenerative Medicine Using Low Molecular Weight Compounds—Differentiation Induction of Insulin-Producing Cells by Physiologically Active Substances," Decomposition and Regeneration, ed. by Hayato Kosuge, Keio University Press, 2004, pp. 360-361 (5 pages).

Umezawa, K. et al., "Induction of Insulin Production in Rat Pancreatic Acinar Carcinoma Cells by Conophylline," Biomedicine and Pharmacotherapy, Elsevier, Paris, vol. 57, No. 8, Oct. 2003, pp. 341-350.

Van Beek et al., "*Tabernaemontana L.* (Apocynaceae): A Review of Its Taxonomy, Phytochemistry, Ethnobotany and Pharmacology," *Journal of Ethnopharmacology*, 10, 1984(pp. 1-156).

Wang Y, Perfetti R, Greig NH, Holloway HW, DeOre KA, Montrose-Rafizadeh C, Elahi D, Egan JM. Glucagon-like peptide-1 can reverse the age-related decline in glucose tolerance in rats. J Clin Invest 99(12):2883-9, 1997.

Watanabe et al., "Pancreatic Beta-Cell Replication and Amelioration of Surgical Diabetes by Reg Protein," Proc. Natl. Acad. Soc., USA, vol. 91, pp. 3389-3392, 1994.

Yamada et al. (Diabetes 31:749-753, 1982).

Yamamoto et al., "Recombinant Human Betacellulin Promotes the Neogenesis of β-Cells and Ameliorates Glucose Intolerance in Mice With Diabetes Induced by Selective Alloxan Perfusion," *Diabetes*, vol. 49, Dec. 2000, pp. 2021-2027.

Zulewski et al., "Multipotential Nestin-Positive Stem Cells Isolated From Adult Pancreatic Islets Differentiate Ex Vivo Into Pancreatic Endocrine, Exocrine, and Hepatic Phenotypes," *Diabetes*, vol. 50, Mar. 2001, pp. 521-533.

* cited by examiner

Vinblastine(R=CH3)   Vincristine(R=CHO)

Conophylline

Conophyllidine

Conofoline

Conophyllinine

Taberhanine

Pachysiphine

USE OF VINCA ALKALOIDS AND SALTS THEREOF

CROSS REFERENCE TO RELATED APPLICATIONS

This application is a divisional of, and claims the benefit of priority under 35 U.S.C. §120 to, U.S. application Ser. No. 10/556,309, filed Nov. 3, 2006 (now abandoned), the entire contents of which are incorporated herein by reference. In addition, this application claims the benefit of priority to Japanese Patent Application No. 2003-13125, filed May 9, 2003 and Japanese Patent Application No. 2003-373665, filed on Oct. 31, 2003, both of which are incorporated herein by reference.

TECHNICAL FIELD

The present invention relates to the use of vinca alkaloids and their salts. More specifically, the present invention relates to agents that enhance insulin-producing and/or -secreting abilities of non-neoplastic cells derived from the pancreas, therapeutic agents for diabetes, blood glucose level-lowering agents, methods for inducing differentiation of non-neoplastic cells derived from the pancreas, methods for enhancing insulin-producing and/or -secreting abilities of non-neoplastic cells derived from the pancreas, methods for producing pancreas-derived non-neoplastic cells whose insulin-producing ability has been enhanced, methods for culturing non-neoplastic cells derived from the pancreas, methods for producing insulin, pancreas-derived non-neoplastic cells that have been induced to differentiate, and pancreas-derived non-neoplastic cells whose insulin-producing and/or -secreting abilities have been enhanced.

BACKGROUND ART

Diabetes is a disease arising from shortage of blood insulin and impaired insulin function, resulting in increased blood glucose concentrations, accompanied by complications such as neuropathy, visual disturbance, renal damage, etc. About 7 million people are afflicted with diabetes in Japan alone. There are two major types of diabetes: Type 1 diabetes is caused by an autoimmune destruction of insulin-producing pancreatic β cells, resulting in an absolute lack of insulin. On the other hand, type 2 diabetes is caused by the expression of insulin resistance in target tissues, such as muscle, fat, and liver, or by a decrease in blood insulin levels due to a decline in pancreatic β cell function. Thus, it can be said that both type 1 and type 2 result from impaired pancreatic β-cell function.

For treatment of type 1 diabetes, insulin injections are conventionally used to lower blood glucose levels in most cases. It is needless to say that, in such cases, four injections a day are laborious to patients. For treatment of type 2, the PPARγ inhibitor, which reduces insulin resistance, is used in some cases. However, the inhibitor is not very effective and causes obesity as a side effect, as has been pointed out. In other cases, agents such as sulfonylurea, which promotes insulin release from β cells, are used, but they are also not very effective.

Apart from drug dependent treatment, a new treatment by transplantation of cells or tissue has been considered promising as regenerative therapy. If large amounts of cells with insulin-releasing ability can be transplanted into type I diabetes patients, four insulin injections per day can be avoided for a long term. Meanwhile, transplantation of insulin-releasing cells is also effective for type 2 diabetes because, irrespective of insulin resistance in target tissues, normal insulin production suppresses the increase of blood glucose level. It is expected that the efficacy of transplantation is far superior to that of treatment with agents currently used, e.g., sulfonylurea, that induce insulin release from β cells.

Porcine pancreatic cells are expected to be utilized in regenerative therapy for diabetes because of their ease of availability, immunological properties, etc. The technique for collecting large amounts of cells and inducing them to differentiate into insulin producing and releasing cells to a sufficient degree has never been known in any cell system.

Most of pancreatic β cells are generated in the fetal period and then proliferate and differentiate very slowly (Herrera, P. L. et al., Development 127: 2317-2322 (2000)). However, experiments have shown that when the pancreas is damaged β cells actively differentiate and proliferate. Differentiation and proliferation of β cells, together with growth of remnant β cells, occur from pancreatic ductal cells both in adult mice subjected to a 90% partial pancreatectomy and in mice that have developed impaired glucose tolerance due to β cell destruction induced by alloxan. These findings have revealed that stem cells are also present in the adult pancreas and have regenerative capacity (Bonner-Wier S. et al., Diabetes 42: 1715-1720 (2000)). Thus, experiments were performed in which stem cells were isolated from the pancreatic ducts and induced to differentiate into insulin-producing cells (Ramiya, V. K. et al., Nature Med. 6: 278-282 (2000) and Bonner-Weir, S. et al., Proc. Nat. Acad. Sci. USA 97: 7999-800 (2000)). Still, a marker of pancreatic stem cells was not known. It was reported last year that nestin, a marker expressed in neural precursor cells, is a marker of pancreatic stem cells, and nestin was confirmed to be expressed in adult pancreatic duct. (Hunziker, E. et al., Biochem. Biophys. Res. Commun. 271: 116-119 (2000)). Furthermore, in vitro culture and differentiation into cells with phenotype including that of insulin-producing cells was succeeded (Zulewski, H. et al., Diabetes 50: 521-533 (2001)). In addition, differentiation of ES cells into pancreatic inlet-like tissues was also succeeded (Lumelysky, N. et al., Science 292: 1389-1394 (2001)). These techniques are expected to be clinically applied in regenerative medicine of the pancreas.

While studies are under way on cells that can potentially serve as materials for pancreatic β cells, physiologically active substances that induce differentiation of pancreatic β cells are considered promising for clinical application in the field of regenerative medicine. Examples of substances that have thus far been known as inducers of differentiation into β cells include activin A, which belongs to the TGF-β superfamily (Demeterco, C. J. et al., Clin. Endo. 85: 3892-3897 (2000)); betacellulin (BTC), which belongs to the EGF family (Ishiyama, N. et al., Diabetologia 41: 623-628 (1998) and Yamamoto, K. et al., Diabetes 49: 2021-2027 (2000); hepatocyte growth factor (HGF) (Ocana, A. G. et al., J. Bio. Chem. 275: 1226-1232 (2000)); basic fibroblast growth factor (bFGF) (Assady, S. et al., Diabetes 50: 1691-1697 (2001)); etc. These substances are proteins, which are not suitable for oral administration. Further, it is difficult to introduce such substances by means of injection because of their immunological problem and instability.

Meanwhile, it has been reported that among low-molecular-weight compounds, nicotinamide acts as a poly (ADP-ribose) synthetase inhibitor, promoting regeneration of pancreatic β cells (Watanabe, T. et al., Proc. Natl. Acad. Sci. USA 91: 3589-3592 (1994) and Sjoholm, A. et al., Endocrinology 135: 1559-1565 (1994)). In addition, nicotinamide has also been reported to promote the expression of Reg protein (Watanabe, T. et al., Proc. Natl. Acad. Sci. USA 91: 3589-3592

(1994)), which promotes the proliferation and differentiation of pancreatic β cells (Akiyama, T. et al., Proc. Natl. Acad. Sci. USA 98: 48-53 (2001)). In another report, fetal porcine pancreatic islet-like cell clusters (ICCs) were induced to differentiate into insulin-producing cells using sodium butyrate and dexamethasone (Korsgren, O. et al., Ups J. Med. Sci. 98: 39-52 (1993)), but the technology is less likely to be put into practical use because of the low specificity.

Meanwhile, the structures of conophylline (Umezawa, K. et al., Anticancer Res. 14: 2413-2418 (1994)) and conophyllidine (Kam, T. S. et al., J. Nat. Prod. 56: 1865-1871 (1993)), both of which are alkaloids isolated from leaves of an Apocynaceae family plant grown in Malaysia and Thailand are known, as shown in FIG. 1. Conophylline is known to exhibit anti-tumor activity in animals (Umezawa, K. et al., Drugs Exptl. Clin. Res. 22: 35-40 (1996)).

It is also known that conophylline induces insulin production of pancreatic acinar carcinoma AR42 J-B13 cells. (The Book of Abstracts (01-21) of the 45th Annual Meeting of the Japan Diabetes Society held in Tokyo, May 18, 2002). However, these cancer cells did not release insulin into culture medium.

The object of the present invention is to provide agents capable of inducing insulin production and/or secretion of non-neoplastic cells derived from the pancreas.

DISCLOSURE OF THE INVENTION

The present inventors have intensively studied to solve the above-mentioned problems and, as a result, found that vinca alkaloids markedly induce differentiation of normal pancreatic cells into insulin-producing and -releasing cells in vitro. Thus, the present invention has been accomplished.

The following summarizes the present invention.

1. An agent for increasing insulin-producing ability of a non-neoplastic cell derived from the pancreas, containing a vinca alkaloid or its pharmacologically acceptable salt as an active ingredient. A preferred example of the aforementioned vinca alkaloid is conophylline. The agent preferably further contains nicotinamide, or nicotinamide and hepatocyte growth factor (HGF).
2. An agent for increasing insulin-secreting ability of a non-neoplastic cell derived from the pancreas, containing a vinca alkaloid or its pharmacologically acceptable salt and nicotinamide as active ingredients. A preferred example of the aforementioned vinca alkaloid is conophylline. The agent preferably further contains hepatocyte growth factor (HGF).
3. A preventive and/or a therapeutic agent for a disease associated with lack of insulin, containing a vinca alkaloid or its pharmacologically acceptable salt as an active ingredient. A preferred example of the aforementioned vinca alkaloid is conophylline. The disease associated with lack of insulin is selected from the group consisting of diabetes, arteriosclerosis, and a complication resulting from these diseases. The preventive and/or the therapeutic agent for a disease associated with lack of insulin preferably further contains nicotinamide, or nicotinamide and hepatocyte growth factor (HGF).
4. A blood glucose level-lowering agent containing a vinca alkaloid or its pharmacologically acceptable salt as an active ingredient. A preferred example of the aforementioned vinca alkaloid is conophylline. The blood glucose level-lowering agent preferably further contains nicotinamide, or nicotinamide and hepatocyte growth factor (HGF).
5. An agent for inducing differentiation from a non-neoplastic cell derived from the pancreas into an insulin-producing cell, containing a vinca alkaloid or its pharmacologically acceptable salt as an active ingredient. A preferred example of the aforementioned vinca alkaloid is conophylline. The agent for inducing differentiation preferably further contains nicotinamide, or nicotinamide and hepatocyte growth factor (HGF).
6. An agent for inducing differentiation from a non-neoplastic cell derived from the pancreas into an insulin-secreting cell, containing a vinca alkaloid or its pharmacologically acceptable salt and nicotinamide as active ingredients. A preferred example of the aforementioned vinca alkaloid is conophylline. The agent for inducing differentiation preferably further contains nicotinamide, or nicotinamide and hepatocyte growth factor (HGF).
7. An agent for promoting induction of differentiation from a non-neoplastic cell derived from the pancreas into an insulin-producing cell, consisting of a vinca alkaloid or its pharmacologically acceptable salt. A preferred example of the aforementioned vinca alkaloid is conophylline.
8. A method for inducing differentiation of a non-neoplastic cell, in which a vinca alkaloid or its pharmacologically acceptable salt is added when the non-neoplastic cell derived from the pancreas is cultured. In this manner, by culturing non-neoplastic cells derived from the pancreas in the presence of a vinca alkaloid or its pharmacologically acceptable salt, the non-neoplastic cell derived from the pancreas differentiate into an insulin-producing cell or an insulin-secreting cell. In induction of differentiation of a non-neoplastic cell derived from the pancreas, nicotinamide, or nicotinamide and hepatocyte growth factor (HGF) are preferably used. A preferred example of the aforementioned vinca alkaloid is conophylline.
9. A method for increasing insulin-producing ability of a non-neoplastic cell derived from the pancreas, in which a vinca alkaloid or its pharmacologically acceptable salt is added when the non-neoplastic cell derived from the pancreas is cultured. A preferred example of the aforementioned vinca alkaloid is conophylline. To increase insulin-producing ability of the non-neoplastic cell derived from the pancreas, nicotinamide, or nicotinamide and hepatocyte growth factor (HGF) are preferably used.
10. A method for increasing insulin-secreting ability of a non-neoplastic cell derived from the pancreas, in which a vinca alkaloid or its pharmacologically acceptable salt is added when the non-neoplastic cell derived from the pancreas is cultured. A preferred example of the aforementioned vinca alkaloid is conophylline. To increase insulin-secreting ability of the non-neoplastic cell derived from the pancreas, it is preferable to use nicotinamide, or nicotinamide and hepatocyte growth factor (HGF).
11. A method for producing a pancreas-derived non-neoplastic cell whose insulin-producing and/or secreting abilities have been increased, which includes culturing the non-neoplastic cells derived from the pancreas in the presence of a vinca alkaloid or its pharmacologically acceptable salt. In this manner, by culturing a non-neoplastic cell derived from the pancreas in the presence of vinca alkaloid or its pharmacologically acceptable salt, it is possible to produce a pancreas-derived non-neoplastic cell whose insulin-producing ability has been increased (an insulin-producing cell) or a pancreas-derived non-neoplastic cell whose insulin-secreting ability has been increased (an insulin-secreting cell). In induction of differentiation of a non-neoplastic cell derived from the pancreas, it is preferable to use nicotinamide, or nicotinamide and hepatocyte growth factor (HGF). A preferred example of the aforementioned vinca alkaloid is conophylline.
12. A method for producing insulin, which includes culturing a non-neoplastic cell derived from the pancreas in the presence of vinca alkaloid or its pharmacologically acceptable salt and nicotinamide and isolating and purifying insulin from a culture (the cultured cell or a medium). A preferred example of the aforementioned vinca alkaloid is conophylline.

13. A method for producing insulin, which includes culturing a non-neoplastic cell derived from the pancreas in the presence of conophylline or its pharmacologically acceptable salt, nicotinamide, and hepatocyte growth factor (HGF) and isolating and purifying insulin from the cultured cell or a medium. A preferred example of the aforementioned vinca alkaloid is conophylline.

14. A pancreas-derived non-neoplastic cell (an insulin-producing cell or an insulin-secreting cell) that has been induced to differentiate by the method of 8 described above.

15. A pancreas-derived non-neoplastic cell whose insulin-producing ability has been increased by the method of 9 described above.

16. A pancreas-derived non-neoplastic cell whose insulin-secreting ability has been increased by the method of 10 described above.

17. A preventive and/or a therapeutic method for a disease associated with lack of insulin, which uses a vinca alkaloid or its pharmacologically acceptable salt. A preferred example of the aforementioned vinca alkaloid is conophylline. The disease associated with lack of insulin is selected from the group consisting of diabetes, arteriosclerosis, and a complication resulting from these diseases. The preventive and/or the therapeutic agent for a disease associated with lack of insulin preferably further contains nicotinamide, or nicotinamide and hepatocyte growth factor (HGF).

18. A preventive and/or a therapeutic method for a disease associated with lack of insulin, which includes culturing a non-neoplastic cell derived from the pancreas in the presence of a vinca alkaloid or its pharmacologically acceptable salt and nicotinamide; and using the cultured non-neoplastic cell derived from the pancreas. Alternatively, the method may include culturing a non-neoplastic cell derived from the pancreas in the presence of a vinca alkaloid or its pharmacologically acceptable salt, nicotinamide, and hepatocyte growth factor (HGF); and using the cultured non-neoplastic cell derived from the pancreas. A preferred example of the aforementioned vinca alkaloid is conophylline. The disease associated with lack of insulin is selected from the group consisting of diabetes, arteriosclerosis, and a complication resulting from these diseases.

"Vinca alkaloids" as used herein refer to vinblastine and vincristine isolated from Vincarosea, an Apocynaceae family plant, and to alkaloids containing the backbone represented by the following structural formula:

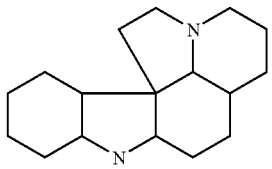 [SMILES: C1CCC2C(C1)NC1CCC3CCCN4CCC12C34]

It should be noted that alkaloids refer to cyclic compounds produced by plants with a nitrogen atom (N) in the ring. Specific examples of vinca alkaloids include, but not limited to vinblastine, vincristine, conophylline, conophyllidine, conofoline, conophyllinine, taberhanine, pachysiphine etc., as shown in FIG. 1.

"Non-neoplastic cells derived from the pancreas" as used herein refer to cells without tumorigenicity that are derived from the pancreas of individual organisms. Such cells include those harvested from the pancreas of organisms and those cultivated from the harvested cells (i.e., cultured cells). Cultured cells include both primary cultured cells and successively transferred cells.

"To increase insulin-producing ability and/or -secreting abilities of cells" is a concept including both causing cells that do not have insulin-producing and/or -secreting abilities to acquire insulin-producing and/or -secreting abilities and causing cells that have insulin-producing and/or -secreting abilities to enhance their insulin-producing and/or -secretion abilities.

"To differentiate into β cells" as used herein means that progenitor cells of β cells come to produce and secrete insulin.

As mentioned earlier, it is known that conophylline, a kind of vinca alkaloid, induces insulin production of pancreatic acinar carcinoma AR42 J-B13 cells, but the AR42 cells were found to be incapable of releasing insulin out of cells, though they do produce insulin. It was unpredictable that, under conditions in which only such weak effects are known, a vinca alkaloid induces insulin production, and further, can even release insulin out of cells when non-neoplastic cells derived from the pancreas were used instead.

Activin, which is capable of inducing AR42J cells to produce insulin, does not exhibit the effect on porcine pancreatic cells. To induce ES cells to produce insulin, many factors including leukocyte activating factor (LAF) as well as many processes are required. The conditions under which cells are induced to differentiate are different depending on the individual cell type. For this reason, even those skilled in the art could not predict that a vinca alkaloid increases insulin production of non-neoplastic cells derived from pancreas and induces insulin to be secreted out of the cells.

Furthermore, since AR42J cells were cancer cells, they could not be used for regenerative medicine from the viewpoint of safety even if their insulin-producing ability was increased. The technique of increasing insulin-producing and -secreting abilities of non-neoplastic cells derived from the pancreas has been established by the present invention, which has made it possible to prepare large amounts of cells available for regenerative medicine.

BEST MODE FOR CARRYING OUT THE INVENTION

Embodiments of the present invention accomplished based on the above-described findings are hereinafter described in detail by giving Examples. Unless otherwise explained, methods described in standard sets of protocols such as J. Sambrook and E. F. Fritsch & T. Maniatis (Ed.), "Molecular Cloning, a Laboratory Manual (3rd edition), Cold Spring Harbor Press and Cold Spring Harbor, N.Y. (2001); and F. M. Ausubel, R. Brent, R. E. Kingston, D. D. Moore, J. G. Seidman, J. A. Smith, and K. Struhl (Ed.), "Current Protocols in Molecular Biology," John Wiley. & Sons Ltd., or alternatively, modified/changed methods from these are used. When using commercial reagent kits and measuring apparatus, unless otherwise explained, attached protocols to them are used.

The objective, characteristics, and advantages of the present invention as well as the idea thereof will be apparent to those skilled in the art from the descriptions given herein. It is to be understood that the embodiments and specific examples of the invention described hereinbelow are to be taken as preferred examples of the present invention. These descriptions are for illustrative and explanatory purposes only and are not intended to limit the invention to these embodiments or examples. It is further apparent to those skilled in the art that various changes and modifications may be made based on the descriptions given herein within the intent and scope of the present invention disclosed herein.

One aspect of the present invention is hereinafter explained in detail.

1. Manufacture of Vinca Alkaloids and Their Salt

Figure 1:
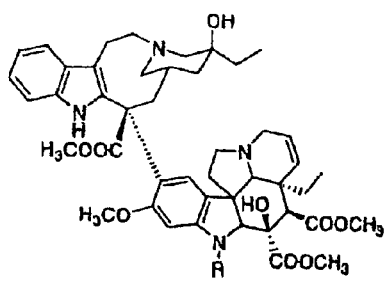
FIG. 1 shows the chemical structural formulae of several compounds belonging to the vinca alkaloid family.
Figure 1:
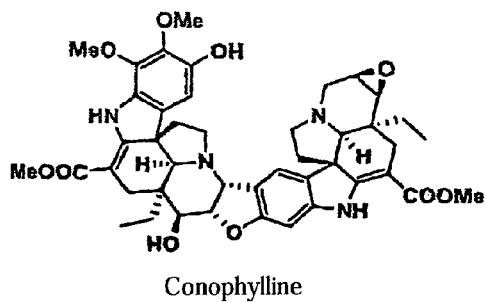
Figure 1:
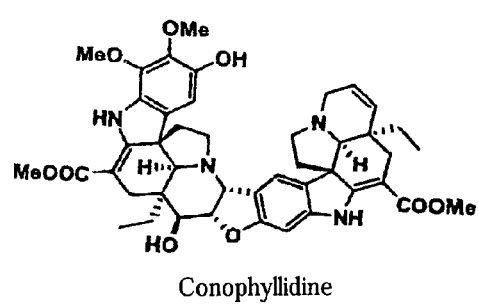
Figure 1:
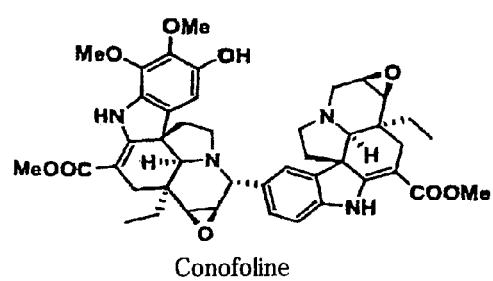
Figure 1:
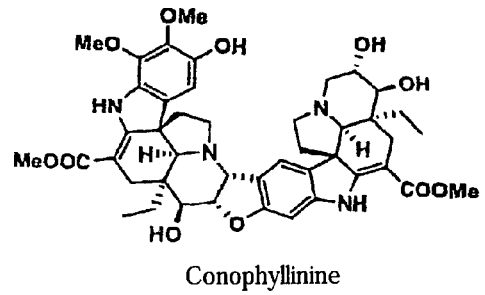
Figure 1:
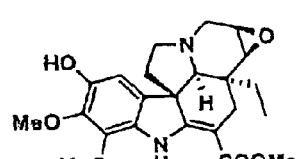
Figure 1:
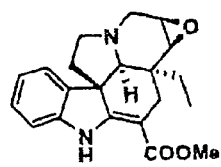

The chemical structural formulae of some compounds belonging to the vinca alkaloid family are shown in FIG. 1.

Vinblastine and vincristine can be isolated and purified from *Vinca rosea* Linn by the method described in Neuss N, Gorman M, Hargrove W, et al., & Manning R E (1964) J. Am. Chem. Soc. 86: 1440-1442, Conophylline can be isolated and purified from leaves of *Ervatamia microphylla*, an Apocynaceae family plant, in the manner as will be described later in Production example 1 (a method modified from Umezawa, K. et al. Anticancer Res. 14: 2413-2418 (1994)). About 4 kg of *Ervatamia microphylla* leaves yields about 500 mg of conophylline crystals.

Conophyllidine can be prepared from leaves of *Ervatamia microphillae* in the same manner as conophylline (Kam, T. S. et al. J. Nat. Prod. 56: 1865-1871 (1993)).

Conofoline and pachysiphine can be prepared by the methods described in Kam T S, Anuradha S. Alkaloids from *Tabernaemontana divaricata*, and Phytochemistry (1995) 40: 313-6.

Conophyllinine and taberhanine can be prepared by the methods described in Kam T S, Pang H S, Lim T M, Biologically active indole and bisindole alkaloids from *Tabernaemontana divaricata*. Org. Biomol. Chem. (2003) 21; 1(8): 1292-7.

Examples of salts of vinca alkaloids include hydrochlorides and sulphates, which are pharmacologically acceptable. These salts can be produce by known methods.

2. Induction of Insulin Production in Non-Neoplastic Cells Derived from the Pancreas by Vinca Alkaloids and their Salts First, non-neoplastic cells derived from the pancreas are prepared. Non-neoplastic cells derived from the pancreas may be derived from mammals. Such mammals include primates, such as humans and monkeys, as well as non-primates, such as pigs, cattle, dogs, and rats. Cells may be derived from healthy animals or from patients who need treatment. Patients are not limited to humans; they may be unhealthy non-human animals. When non-neoplastic cells derived from a healthy animal are used, preferred animals are fetuses and neonates (for example, in the case of pigs, neonatal pigs within 3 days of birth). Non-neoplastic cells may be exocrine cells or endocrine cells, but endocrine cells are preferred. Further, among endocrine cells, $\beta$ cells and their progenitor cells are more preferred.

Isolation of non-neoplastic cells from the pancreas of healthy mammalian animals may be performed, for example, as follows: The pancreas is removed from a mammal and connective tissue is detached. The pancreas is dissected, buffer is added, and the mixture is stirred. After stirring, the supernatant is discarded, an enzyme Liberase is added, and the mixture is stirred again. Subsequently, a cycle of centrifugation, discarding of the supernatant, and addition of PBS is repeated. Cells are suspended with PBS and this cell suspension is overlaid on Histopaque, followed by centrifugation. Since pancreatic endocrine cells forms a belt-like white layer at the interface between cell suspension and Histopaque, this layer is harvested. The sample is centrifuged and the supernatant is discarded. The cells is suspended in medium and transferred to the culture chamber to be incubated. Subsequently, spheroids (loose cell aggregates) are formed by stirring for an appropriate time, followed by incubation. Cells detached from the chamber and floating in the medium are used for the subsequent operations.

The cells floating in the culture chamber are transferred to the centrifuge tube, which is let to stand still until spheroids have sunk to the bottom. Then the supernatant is discarded and medium was added, followed by light shaking. The tube is let to stand still and the spheroids are allowed to settle down to the bottom. After this operation is repeated 2 or 3 times, the cell lysate is centrifuged and the supernatant is discarded. The residual cells are cultured under the condition of 5% $CO_2$ and 37° C. in medium supplemented with a vinca alkaloid or its pharmacologically acceptable salt. The culture may be stationary culture. Examples of suitable media include RPMI medium etc. It is also more preferable to add nicotinamide and hepatocyte growth factor (HGF) in addition to a vinca alkaloid or its pharmacologically acceptable salt. The medium may be changed every 4 to 7 days and the culture is incubated for 7 to 35 days. The morphology of the cells may be examined at suitable time intervals during the incubation period. Further, when the medium is changed, the culture solution may be recovered and subjected to the measurement of the insulin amount in the medium.

The methods for separating and culturing cells described above can also be applied when non-neoplastic cells derived from patients' pancreas are prepared. It should be noted that, to obtain non-neoplastic cells derived from patients' pancreas, a method is suggested in which tissue fragments are harvested from patients' pancreas so that non-neoplastic cells are isolated from these tissue fragments by the above-described methods.

As thus far described, by culturing non-neoplastic cells derived from the pancreas in the presence of a vinca alkaloid or its salt, differentiation of non-neoplastic cells derived from the pancreas can be induced. Preferably, non-neoplastic cells derived from the pancreas can be induced to differentiate into insulin-producing and -releasing cells (e.g., $\beta$ cells). Furthermore, insulin-producing and/or -secreting abilities of normal pancreatic cells can be increased. Furthermore, by culturing non-neoplastic cells derived from the pancreas in the presence of a vinca alkaloid or its salt, insulin can be isolated and purified from cultures (cultured cells or a medium) by known methods.

The pancreas-derived non-neoplastic cells whose insulin-producing and/or -secreting abilities have been increased by culturing in the presence of a vinca alkaloid or its salt are capable of producing 10 ng or more, preferably 25 ng or more, and more preferably 55 ng or more in 1 ml of medium when they were cultured at the concentration of $2.5\times10^5$ cells per 1 ml of medium for 7 to 35 days.

As mentioned earlier, porcine pancreatic cells are expected to be used in regenerative therapy for diabetes because of their ease of availability, immunological properties, etc. The method for collecting large amounts of cells to induce them to differentiate into insulin-producing and -releasing cells to a sufficient degree has never been known in any cell system.

The technique according to the present invention makes it possible to induce large amounts of cells to differentiate into insulin-producing and -releasing cells to a sufficient degree. Accordingly, insulin-producing and -releasing cells obtained by the methods according to the present invention can be used in regenerative medicine for diabetes.

Insulin-producing and -releasing cells obtained by the methods according to the present invention may be suspended in a solution and/or embedded in a support matrix and then administered to subjects. The solution in which insulin-producing and -releasing cells are suspended may be a pharmacologically acceptable carrier and diluent, such as saline, a buffer solution, etc. To the solution, a preservative (e.g., p-hydroxybenzoic acid ester, chlorobutanol, thiromesal, etc.) and a stabilizer (e.g., L-arcorbic acid, etc.) may be added. After insulin-producing and -releasing cells are suspended in the solution, they may be subjected to a sterilization treatment. A support matrix in which insulin-producing and -releasing cells are embedded may be a matrix that is recipient-compatible and that degrades into a product not harmful to the recipient. Materials for the matrix may include natural polymers, synthetic polymers, etc. Examples of natural polymers include collagen, gelatin, etc. Examples of synthetic polymers include polyglycolic acid, polylactic acid, etc. The matrix can be in the form of, but not limited to, film, sheet, particle, paste, etc.

3. Agents and Drugs Based on Vinca Alkaloids

Vinca alkaloids and their pharmacologically acceptable salts can increase insulin-producing and/or -secreting abilities of non-neoplastic cells derived from the pancreas. Further, vinca alkaloids and their pharmacologically acceptable salts can also decrease blood glucose levels. Therefore, these compounds may be administered to human and other animals as drugs (e.g., therapeutic agents for diabetes) or may be used as reagents in experiments. These compounds may be used alone or in combination with other agents (e.g., other therapeutic agents for diabetes). It should be noted that, when a vinca alkaloid has been administered to an animal, its effect is likely to have been enhanced by taking advantage of endogenous nicotinamide and/or an endogenous hepatocyte growth factor (HGF); thus, in administering a vinca alkaloid, nicotinamide and/or hepatocyte growth factor (HGF) may be simultaneously administered.

When administered to humans, a vinca alkaloid or its pharmacologically acceptable salt may be administered orally. The dosage is, for example, 0.1 to 10 mg/kg bw daily in a single dose or divided doses. However, the amount of a dose and number of administration can be suitably changed depending on the symptoms, age, dosage regimen, etc.

Vinca alkaloids and their pharmacologically acceptable salts may be administered orally in preparations, such as tablets, capsules, granule, powder, syrups, etc. Alternatively, they may be administered parenterally by intraperitoneal or intravenous injection in preparations such as injectable formulations, suppositories, etc. The content of a vinca alkaloid or its pharmacologically acceptable salt (active ingredient) in a preparation can vary between 1 to 90% by weight. For example, when the preparation is in the form of a tablet, a capsule, a granule, a powder, etc. the content of an active ingredient is preferably 5 to 80% by weight. In the case of a liquid preparation such as syrup, the content of an active ingredient is preferably 1 to 30% by weight. In addition, in the case of an injectable preparation for parenteral administration, the content of an active ingredient is preferably 1 to 10% by weight.

Vinca alkaloids and their pharmacologically acceptable salts are formulated by known methods using the following formulation additives: excipients (sugars such as lactose, sucrose, glucose, and mannitol; starches such as potato, wheat, and corn; inorganic substances such as calcium carbonate, calcium sulfate, and sodium hydrocarbonate; cellulose crystal; etc.), binders (starch-paste liquid, gum arabic, gelatin, sodium arginate, methylcellulose, ethylcellulose, polyvinylpyrrolidone, polyvinyl alcohol, hydroxypropylcellulose, carmellose, etc.), lubricants (magnesium stearate, talc, hydrogenerated vegetable oil, macrogol, and silicone oil), disintegrators (starch, agar, gelatin powder, cellulose crystal, sodium carboxymethylcellulose, calcium carboxymethylcellulose, calcium carbonate, sodium hydrocarbonate, sodium arginate, etc.), correctives (lactose, sucrose, glucose, mannitol, fragrant essential oils, etc.), solvents (water for injection, sterile purified water, sesame oil, soybean oil, corn oil, olive oil, cottonseed oil, etc.), stabilizers (inert gases such as nitrogen and carbon dioxide; chelating agents such as EDTA and thioglycolic acid; reducing substances such as sodium bissulfite, sodium thiosulfate, L-ascorbic acid, and rongalite; etc.), preservatives (paraoxybenzoic acid, chlorobutanol, benzyl alcohol, phenol, benzalkonium chloride, etc.), detergents (hydrogenated castor oil, polysorbates 80 and 20, etc.), buffers (sodium salts of citric acid, acetic acid, and phosphoric acid; boric acid; etc.), diluents, etc.

Vinca alkaloids and their pharmacologically acceptable salts can be used to prevent and/or treat diseases (e.g., diabetes and arteriosclerosis) associated with lack of insulin. Vinca alkaloids and their pharmacologically acceptable salts can also be used in studies of insulin production and/or secretion of pancreatic cells. Vinca alkaloids and their pharmacologically acceptable salt can further be used for blood glucose level-lowering agents as well as for therapeutic agents for complications resulting from prolonged high blood glucose levels, such as retinopathy of the eyes, nephropathy, neuropathy, gangrene, arteriosclerosis, etc.

Hereinafter, the present invention will be explained in more detail with reference to Production examples and Experiment examples. These Production examples and Experiment examples are for explanatory purposes only and are not intended in any way to limit the scope of the invention.

The materials used in the example and their suppliers are as follows.
Neonatal pigs: Takayama Pig Farm
Roswell Park Memorial Institute (RPMI) medium: Invitrogen
Nicotinamide: Sigma Chemical Science (Sigma)
Fetal bovine serum (FBS): Sigma
Phosphate buffered saline (PBS)
Histopaque: Sigma
Hepatocyte growth factor (HGF): Sigma Chemical Science
DMEM: Nissui Pharmaceutical Co., Ltd.
HEPES: Sigma
Kanamycin: Sigma
Glutamine: Sigma
Penicillin G: Sigma
Trypsin: Wako
EDTA: Kanto Chemical Co., Inc.
PBS⁻ for fluorescent antibodies
Bovine serum albmine (BSA): Sigma Anti-insulin antibody: Biogenesis
Cy3-conjugated anti-guinea pig antibody: Jackson ImmunoResearch Laboratories, Inc. (West Grove, Pa.)
Activin A: R&D Systems, Inc. (Minneapolis, Mo.)
Hoechst 33258: Polysciences, Inc.

EXAMPLE 1

Production Example 1

Preparation of Conophylline

Conophylline was isolated and purified from leaves of *Ervatamia microphylla*, an Apocynaceae family plant, (harvested in Khon Khen, Thailand) in the following manner.

Active substance was extracted from about 4 kg of *Ervatamia micorophylla* leaves with 100 L of chloroform to afford about 130 g of oily substance. This oily substance was chromatographed on a silica gel column (purification was performed by a total of 5 rounds of column chromatography using about 500 g of silica gel), eluting sequentially with chloroform:methanol (40:1 and 20:1). Subsequently, using morphological changes of K-ras-NRK cells as an activity marker, the fractions exhibiting this biological activity were recovered. The crude purified product obtained (about 40 g) was chromatographed on a silica gel column with n-hexane:ethyl acetate (1:2 and 0:1) (using about 500 g of silica gel; purchased from Merck Co.) to afford 1.5 g of active fractions. The active fractions were then chromatographed on a silica gel column (using 150 g of silica gel) with n-hexane:ethyl acetate:chloroform (9:3:1 and 6:3:1), active fractions were recovered, and concentrated to afford about 500 mg of crystals. The resulting conophylline was confirmed by mass spectrometry and NMR spectrometry comparing its data with the literature data (Umezawa, K. et al., Anticancer Res. 14: 2413-2418 (1994)). The solvents used were purchased from Kanto Chemical Co., Inc.

EXAMPLE 2

Experiment Examples I and II

1. Methods

Neonatal pigs within 72 hours of birth were obtained from the (Takayama) pig farm. The whole pancreas (ventral and dorsal pancreas) was removed under general anesthesia immediately after animals were brought to the operating room. After elimination of connective tissue covering the removed pancreas and blood adhering to it, the pancreas was transferred to a 10 ml beaker and dissected into small pieces with ophthalmic scissors. The dissected pieces were transferred to a 100 ml conical flask, to which 50 to 60 ml of phosphate buffered saline (PBS) was added. After a 3 min rotation at 110 rpm on a low speed stirrer, the mixture was allowed to stand still and the supernatant was discarded. Then, 40 mL of phosphate buffered saline containing Liberase PI (Roche) at a concentration of 2.5 mg/ml was added. After an 8 min rotation at 110 rpm on a low speed stirrer, the mixture was allowed to stand still and the supernatant containing the cells was collected. The operation was repeated 5 times. The supernatant collected was centrifuged at 1200 rpm for 5 min. to collect cells. The cells collected in the centrifugal sedimentum was suspended in 25 to 50 ml of PBS, 25 ml of cell suspension was overlaid gently on 10 ml of Histopaque 1077 (Sigma), followed by centrifugation at 1800 rpm for 10 min. Pancreatic (endocrine) cells form a band-like white layer at the interface between cell suspension and Histopaque (cell separation and purification methods)

Cells present at the interface are recovered with a Pasteur pipette, suspended in RPMI 1640 supplemented with 10 mM Nicotinamide and 10% heat-inactivated FBS, collected by centrifugation at 1200 rpm for 5 min. These cells were resuspended in the same medium and then subjected to stationary culture in a 75 ml culture flask (5% $CO_2$ incubator, 37° C.) for a whole day and night.

Culture Conditions:

Cells floating in the flask were removed, and cells adhering to the bottom were detached with EDTA-Trypsin and collected. Cells were suspended in each of media (groups 1 to 8) and stationary culture was performed by plating cells (1.25× $10^3$ cells/ml) in culture chambers (2 ml each; 5% $CO_2$-incubator, 37° C.).

Media Group
1: RPMI 1640 with 10% FBS (Control)
2: Control+10 mM nicotinamide
3: Control+10 ng/ml HGF
4: Control+0.1 µg/ml conophylline
5: 2+3
6: 2+4
7: 3+4
8: 2+3+4

The culture medium was exchanged every four days and the observation was made for three weeks, during which time the morphology of cells was observed every week and the appearance of pancreatic β-cells was confirmed by immunofluorescence using peroxidase (Experiment example 1). Coloration was performed using 3-amino-9-ethyl carbazole (AEC; 0.75 mg/ml) as a substrate. In addition, the medium was recovered every time it was exchanged (every four days) for measurement of the amount of insulin secreted into the medium by ELISA (Experiment example II).

2. Results

Figure 2:
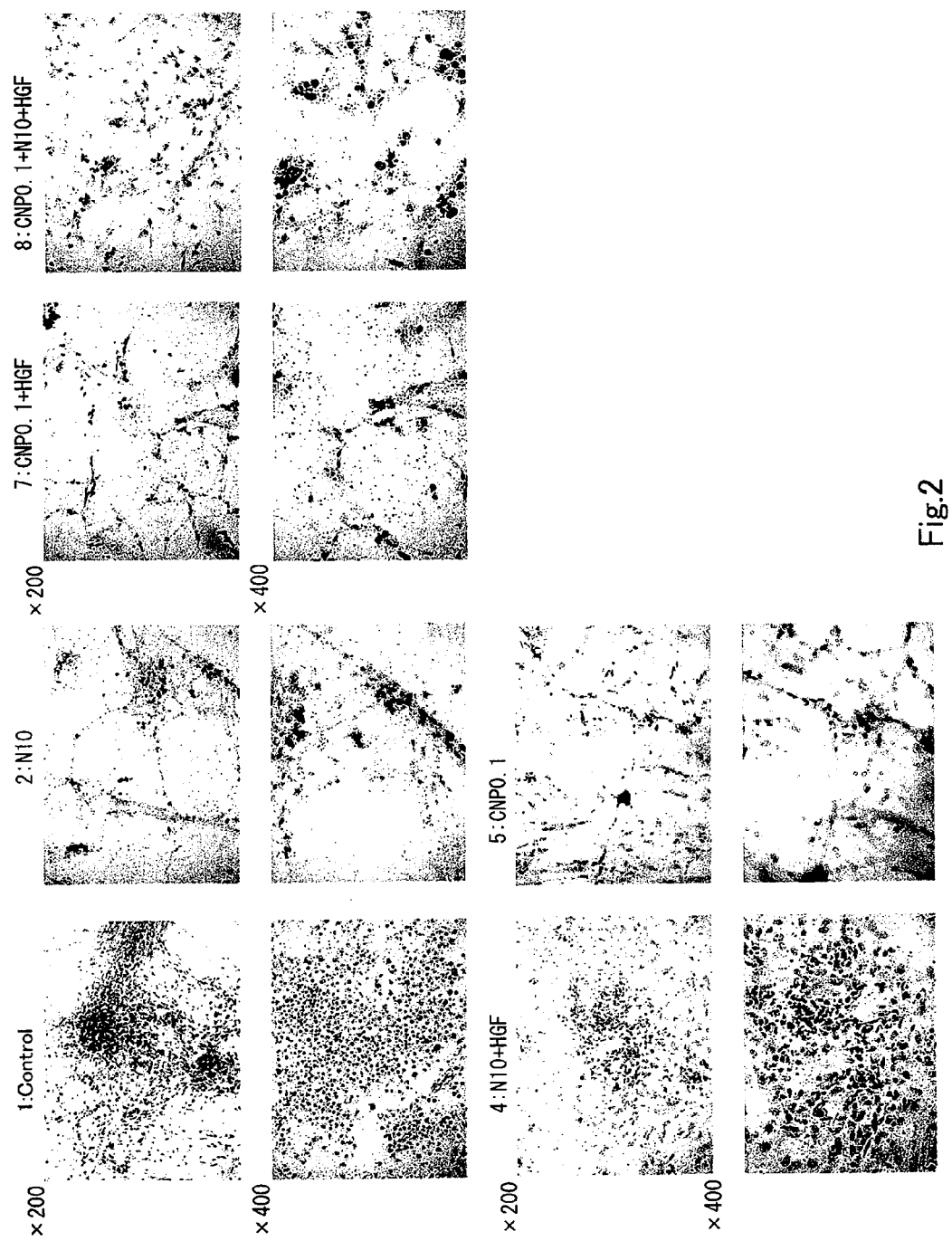
FIG. 2 shows the results of immunostaining of fetal porcine pancreatic cells cultured in media to which the following were added for three weeks: vehicle (1); only nicotinamide (10 mM) (2); nicotinamide (10 mM) and HGF (10 ng/ml) (4); only conophylline (0.1 µg/ml) (5); conophylline (0.1 µg/ml) and HGF (10 ng/ml) (7); conophylline (0.1 µg/ml), nicotinamide (10 mM), and HGF (10 ng/ml) (8). In the figure, N and CNP denote nicotinamide and conophylline, respectively.

FIG. 2 shows the results of Example 1 It has been reported that nicotinamide (Akiyama, T. et al., Proc. Natl. Acad. Sci. USA 98: 48-53 (2001)) and HGF (Ocana, A. G. et al., J. Biol. Chem. 275: 1226-1232 (2000)) promote differentiation of insulin-producing cells in the limited experimental systems, but their effects are weak. As shown in FIG. 2, three weeks later, only a few insulin-producing cells colored in red were seen in vehicle (1), only nicotinamide (10 mM) (2), nicotinamide and HGF (10 ng/ml) (4), only conophylline (0.1 µg/ml) (5), and conophylline and HGF (7). In the triple mixture of nicotinamide, HGF, and conophylline (8), however, the number of insulin-producing cells colored markedly in red increased. It should be noted that the mixture of nicotinamide and conophylline (6) produced a smaller number of insulin-producing cells than the aforementioned triple mixture the mixture (6) did; however, nicotinamide-conophylline mixture had a marked increase in that number, compared with the others (not shown in the figure).

Figure 3:
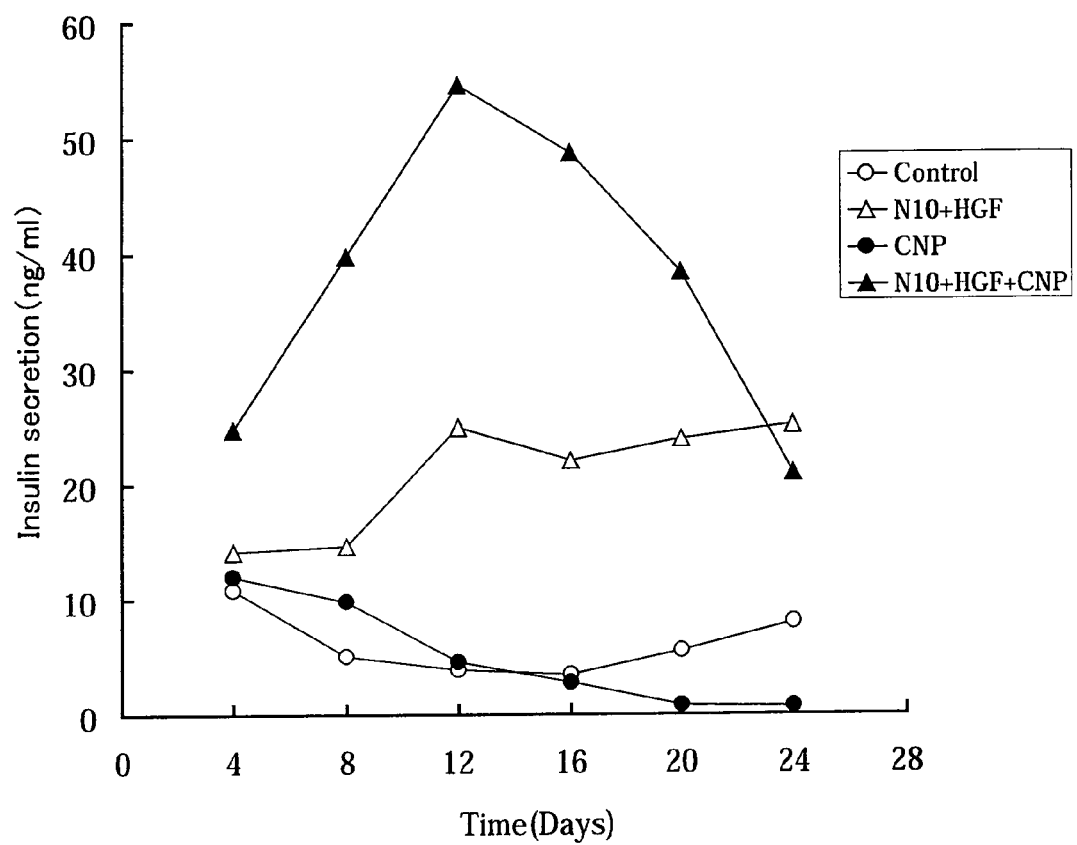
FIG. 3 shows the results of ELISA measurement of the amount of insulin produced by fetal porcine pancreatic cells cultured in media to which the following were added: vehicle (white circle); nicotinamide and HGF (white triangle); only conophylline (black circle); conophylline, nicotinamide, and HGF (black triangle). In the figure, N and CNP denote nicotinamide and conophylline, respectively.

FIG. 3 shows the results of Example II. As indicated in FIG. 3, nicotinamide combined with either HGF or conophylline cultured for 8 to 20 days was able to produce some amount of insulin in the medium. Furthermore, nicotinamide combined with HGF and conophylline had a marked increased in the amount of insulin release, compared with other combinations or alone.

Summary

To date, there have been no techniques for inducing differentiation of insulin-producing cells in pancreatic cells of neonatal pigs. It has been revealed that the combination of nicotinamide, HGF, and conophylline dramatically increases the proportion of insulin-producing cells, thereby resulting in a large amount of insulin release as well. Since the neonatal porcine pancreas can be supplied in large amounts, it will be possible to prepare in large amounts implantable cells that release enough insulin. It is thought that this technique enables regenerative therapy, which is expected for diabetes in the future.

Further, conophyllidine, like conophylline, has been confirmed to induce morphological changes involved in insulin production of pancreatic acinar carcinoma AR42J cells, suggesting that conophyllidine, like conophylline, has the effect of increasing insulin-producing and/or -secreting abilities of non-neoplastic cells derived from the pancreas.

EXAMPLE 3

Comparative Example 1

Effect in which Conophylline Induces Differentiation of Rat Pancreatic Acinar Carcinoma AR42 J-B13 Cells into Insulin-Producing Cells 1. Methods
Cell Culture DMEM was sterilized by filtration after its pH was adjusted to 7.4 in the presence of 20 mM HEPES-NaOH. AR42J-B13 cells (endowed by Dr. Itaru Kojima, Institute for Cellular and Molecular Regulation, Gunma University) a highly sensitive subclone of AR42J, were cultured at 37° C. in a 5% $CO_2$ incubator with 20 ml of culture medium DMEM supplemented with 100 mg/l kanamycin, 0.6 g/l glutamine, 100 unit/ml penicillin G, 5 mM $NaHCO_3$, and 10% FBS. To prevent transformation due to a high density of the cells and to retain differentiation ability of the cells, the cells were transferred every 2 to 3 days to maintain 2.5% to 5% of confluency. The cell transfer was performed as follows: After the medium was removed, the cells were washed twice in PBS$^-$ ($Ca^{2+}$, $Mg^{2+}$-free PBS; 8 g/l, NaCl, 0.2 g/l KCl, 0.916 g/$Na_2HPO_4$, 0.2 g/l $KH_2PO_4$). Subsequently, the cells were detached using 2 ml of trypsin-EDTA solution, and then trypsin was inactivated by addition of 8 ml of the medium. Subsequently, the cell were sedimented by centrifugation at 1000 rpm for 5 min, trypsin was removed, 10 ml of fresh medium was added, and transferred to be 2.5% to 5% of confluency. Cells were cryopreserved under the condition of 7.5% dimethyl sulfoxide (DMSO).

Cells that had been prepared at a density of $4 \times 10^5$ cells/ml were plated at 500 µl per well on 24-well plates, followed by incubation at 37° C. in a 5% $CO_2$ incubator. The next day, either 0.1-0.3 µg/ml conophylline alone or 0.1 µg/ml conophylline plus 100 µM HGF was added. After incubation for an appropriate time at 37° C. in 5% $CO_2$, the medium was removed to a 1.5 ml Eppendorf tube, cells were washed once in 200 µl of PBS$^-$, and then 200 µl of fresh PBS$^-$ was added. The morphology of the viable cells was observed and photographed at 150× magnification with a camera linked to the microscope. Subsequently, cells were detached with trypsin and all the solution was transferred to the aforementioned Eppendorf tube for trypan blue exclusion test. Further, the photograph was enlarged 2.5 times and a morphological change was defined as having occurred when the full length of a cell in the diameter became 1.5 times; thus, the rates of morphological changes were determined.

Immunofluorescence

Cells that had been prepared at a density of $2 \times 10^5$ cells/ml were plated at 500 µl per well on 8-well plates, followed by addition of either 0.1 µg/ml conophylline or 0.1 µg/ml conophylline plus 100 µM HGF. Subsequently, the cells were incubated at 37° C. in a 5% $CO_2$ incubator for 72 hours to differentiate. After the medium was removed, the cells were washed once with PBS$^-$ for fluorescent antibodies (8 g/l NaCl, 50.45 g/l $NaH_2PO_4.2H_2O$, 1.28 g/l $Na_2HPO_4$) and fixed with 3% formaldehyde at 4° C. overnight (or at room temperature for 30 min). Next, the cells were washed twice with PBS$^-$ for fluorescent antibodies and blocked by adding 1 ml of 1% BSA solution (a solution of PBS– for fluorescent antibodies) per well, followed by incubation at room temperature for 1 hour. To quench with 50 mM glycine (a solution of PBS$^-$ for fluorescent antibodies), cells were incubated for 5 min, followed by washing 3 times. Next, the solution in the plastic wells was removed, 50 µl per well of alpha-insulin antibody diluted 100-fold with a 10-fold diluted blocking buffer was placed taking care not to allow cells to dry, and the plates were allowed to stand still at room temperature for 1 hour. Here, a well of cells induced to differentiate with 2 nM activin A and 100 µM HGF was prepared and preserved without primary antibody for the purpose of comparing the influence of the nonspecific binding of the secondary antibody. Next, slides were transferred to the chamber and washed three times with PBS$^-$ for fluorescent antibodies for 5 min while shaking on a shaker. Next, Hoechst 33258 was added to Cy3-conjugated anti-guinea pig antibody diluted 100-fold with a 10-fold diluted blocking solution at a 1:100 dilution, and the antibody was overlaid as was the primary antibody. The slides were shielded from light with aluminum foil, allowed to stand still at room temperature for 1 hour and then placed in the shielded chamber, followed by washing three times for 10 min with TNT buffer (0.1 M Tris-HCl, 0.15 M NaCl, 0.05% Tween 20; pH 7.5) under light shielding on the shaker. The slides were overlaid with 50% glycerol in PBS$^-$, covered with coverslips, and photographed under the microscope.

2. Results

When conophylline was used alone and in combination with HGF, process outgrowth such as that seen in nerve cells was concentration-dependently induced at concentrations of 0.1 to 0.3 µg/ml. Further, combination with HGF slightly enhanced cell death, thereby increasing the rates of morphological changes.

The results of the immunofluorescence revealed the following: After 72 hours, when 100 pM HGF was used alone, no red coloration indicating insulin was observed in cells. When 0.1 µg/ml conophylline and 100 pM HGF were used in combination, however, red coloration of insulin was observed in the cytoplasm excluding the nucleus. Further, the coloration was seen scattered as if insulin was confined in granules in the cytoplasm. No insulin coloration was observed in the vicinity of the cell membrane involved in insulin release. Meanwhile, when 2 nM activin A and 100 pM HGF were used in combination, red coloration of insulin was observed in granules as in combination of conophylline and HGF, but its localization was different: the red coloration was observed along the axis of the process split into two, with some accumulation at the tips of the neurites.

In addition, quantification of insulin secretion of the differentiated cells was attempted using the ELISA method, but the secretion was found to be below the detection level.

Summary

In conclusion, it was revealed that conophylline is capable of inducing morphological changes of ARJ42 cells, thereby inducing ARJ cells to produce insulin, but that conophylline is incapable of inducing insulin secretion out of cells.

EXAMPLE 4

Effect of Lowering Blood Glucose Levels In Vivo by Conophylline

Example 2 revealed that conophylline has the effect of inducing pancreatic cells to produce and release insulin in vitro. To examine whether the administration of conophylline induces insulin production in vivo as well, changes in blood glucose levels caused by the administration of conophylline in vivo were measured.

Figure 4:
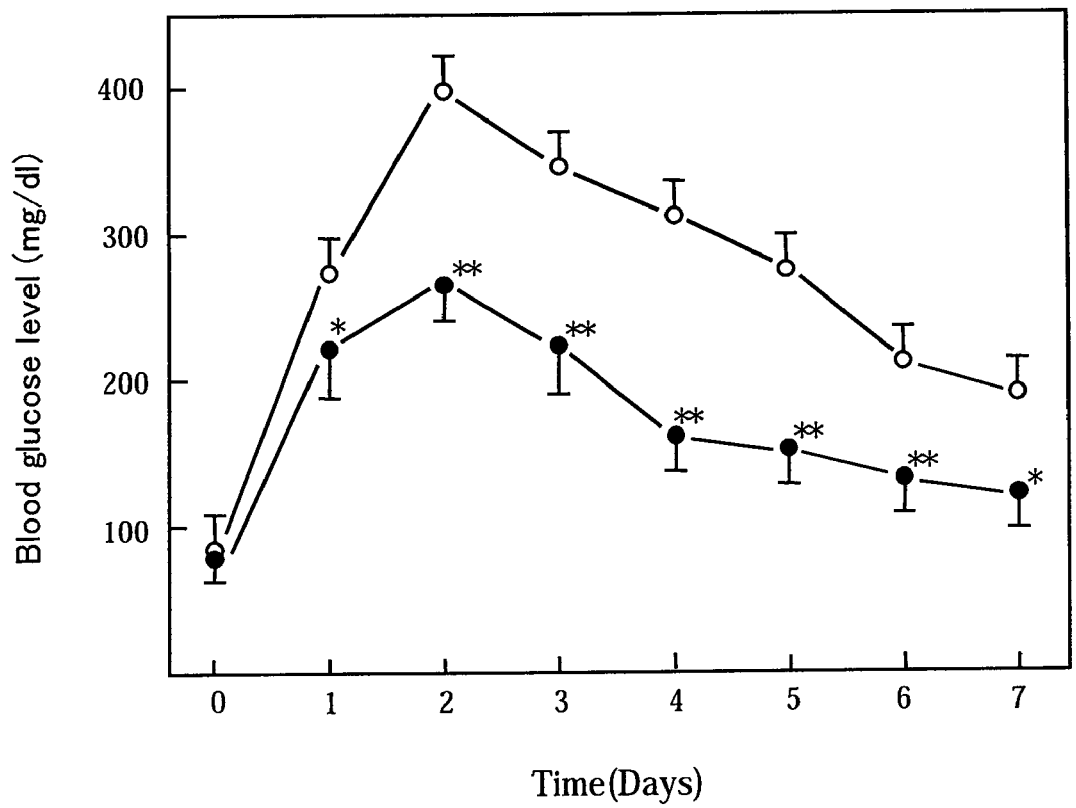
FIG. 4 shows the effect of conophylline on blood glucose levels of streptozotocin-administered rats.

Ten 1-day old Wistar rats (purchased from Japan SLC, Shizuoka, Japan) were intraperitoneally injected with streptozotocin (purchased from Wako Pure Chemical Industries, Ltd., dissolved in 0.05 mM citrate buffer (pH 4.5)) at 85 µg/g BW per rat. Streptozotocin decreases insulin production by destroying pancreatic β cells, thereby inducing diabetes. The day of streptozotocin injection was defined as day 0, Starting from the next day (day 1), five rats were injected subcutaneously with a solution (ethanol) of conophylline at 5 µg/g BW for seven consecutive days and their random blood glucose levels were measured daily. Five rats in the control group received the same volume of solvent (Control). As a result, as shown in FIG. 4, all the rats showed a remarkable increase in blood glucose levels when streptozotocin was administered, whereas the rats administered conophylline (black circle) showed an apparent decrease in blood glucose levels, compared with the control (white circle), indicating the effect of lowering blood glucose levels by conophylline (*: P<0.05, **: P<0.01 vs Control). These findings revealed that conophylline induces insulin production in vivo as well.

In addition, conophylline alone exerted an effect, as compared with the results obtained in vitro. This suggests that when conophylline has been administered into the body, endogenous nicotinamide and/or hepatocyte growth factor (HGF) have been utilized.

INDUSTRIAL APPLICABILITY

Agents capable of inducing insulin production and/or secretion of non-neoplastic cells derived from the pancreas have been provided by the present invention.

The agents according to the present invention can induce differentiation of non-neoplastic cells derived from the pancreas. Further, the agents according to the present invention can increase insulin-producing and/or -secreting abilities of non-neoplastic cells derived from the pancreas.

The invention claimed is:

1. A method for producing an insulin-secreting cell, comprising culturing a non-neoplastic pancreatic endocrine cell derived from the pancreas in medium containing nicotinamide, wherein the medium comprises an effective amount of conophylline or its pharmacologically acceptable salt for enhancing the ability of the nicotinamide to enhance insulin-secreting ability of the cell.

2. The method according to claim 1, wherein the medium further comprises hepatocyte growth factor (HGF).

3. The method according to claim 1, further comprising isolating insulin from the insulin-secreting cell or the medium in which the insulin-secreting cell was cultured.

4. The method according to claim 2, further comprising isolating insulin from the insulin-secreting cell or the medium in which the insulin-secreting cell was cultured.

* * * * *